United States Patent
Kondo et al.

(10) Patent No.: US 7,938,031 B2
(45) Date of Patent: May 10, 2011

(54) FLOW CELL, FLOW CELL MANUFACTURING METHOD AND PARTICLE MEASUREMENT INSTRUMENT

(75) Inventors: Kaoru Kondo, Tokyo (JP); Hiroshi Sugawara, Tokyo (JP); Takashi Futatsuki, Tokyo (JP); Akira Suzuki, Miyagi (JP); Masahiko Tatsumi, Hyogo (JP); Kouki Ogura, Hyogo (JP); Junichi Watanabei, Tokyo (JP)

(73) Assignee: Rion Co., Ltd., Kokubunji-shi, Tokyo (JP)

( * ) Notice: Subject to any disclaimer, the term of this patent is extended or adjusted under 35 U.S.C. 154(b) by 365 days.

(21) Appl. No.: 12/045,717

(22) Filed: Mar. 11, 2008

(65) Prior Publication Data

US 2008/0223154 A1    Sep. 18, 2008

(30) Foreign Application Priority Data

Mar. 12, 2007  (JP) .................................. 2007-061267

(51) Int. Cl.
*G01N 15/00*    (2006.01)

(52) U.S. Cl. ...................................................... 73/865.5
(58) Field of Classification Search .................. None
See application file for complete search history.

(56) References Cited

U.S. PATENT DOCUMENTS

| | | | | |
|---|---|---|---|---|
| 3,999,861 A * | 12/1976 | Bellinger | ...................... | 356/410 |
| 5,036,204 A * | 7/1991 | Leyden | ........................ | 250/373 |
| 5,332,901 A * | 7/1994 | Eckles et al. | .................... | 250/345 |
| 6,199,257 B1 * | 3/2001 | Munk et al. | ..................... | 29/423 |
| 6,281,975 B1 * | 8/2001 | Munk | ........................... | 356/440 |
| 6,307,362 B1 * | 10/2001 | Mangan | ........................ | 324/71.4 |
| 6,482,652 B2 * | 11/2002 | Furlong et al. | .................. | 436/63 |
| 6,603,556 B2 * | 8/2003 | Belz et al. | ..................... | 356/440 |
| 6,731,100 B1 * | 5/2004 | Hansen et al. | ............... | 324/71.4 |
| 6,887,430 B1 * | 5/2005 | Dou et al. | .................. | 422/82.09 |
| 7,544,326 B2 * | 6/2009 | Norton et al. | ................... | 422/73 |

* cited by examiner

*Primary Examiner* — Robert R Raevis
(74) *Attorney, Agent, or Firm* — Lee Fredric Sharra

(57) ABSTRACT

A flow cell 1 is provided with a flow channel 2 which has rounded corners 3 in section. A measuring sample under high pressure is introduced into the flow channel 2 formed in the flow cell 1 and particles existing in the measuring sample are measured. The measuring sample is in a liquid phase, a gaseous phase or a super critical phase above 1 MPa.

5 Claims, 4 Drawing Sheets

FLOW CELL, FLOW CELL MANUFACTURING METHOD AND PARTICLE MEASUREMENT INSTRUMENT

CROSS REFERENCE TO RELATED APPLICATIONS

The present application claims priority under 35 U.S.C. §119, based on the following patent: Japanese Patent Application No. 2007-061267 (Filed on Mar. 12, 2007)

BACKGROUND OF THE INVENTION

1. Field of the Invention

The present invention relates to a flow cell for introducing a sample under high pressure into a measuring instrument, a method for manufacturing the flow cell, and a particle measuring instrument using the flow cell.

2. Description of the Prior Art

A high pressure fluid is used in a material gas used in a production process for an electronic device, compressor air for a machine driven jet gun and the like. A liquid phase, a gaseous phase, and a super critical phase exist in the high pressure fluid. In particular, in the case of the high pressure fluid used in the production process for the electronic device such as a semiconductor, it is required to control small particles contained in the fluid. Under the present circumstances, it is possible to measure the particles up to a pressure of 0.7 MPa using a fine particle measuring instrument which is available in the marketplace. In the case of high pressure gas, the gas is measured by reducing the pressure to 0.7 MPa using a regulator. When the measured particle diameter is large, the particles can be controlled by the compressor air and the like, but, in this case, the pressure is reduced to atmospheric pressure for measurement. Since a sample cannot be measured under a high pressure condition even by a densitometer and a chemical composition analyzer, the pressure must be reduced for measurement.

A flow cell used in a conventional particle measuring instrument is shown in FIG. 7. A flow cell 105 of a rectangle shape is known, of which the flow channel 104 is formed by combining four optically transparent rectangular flat plates 100 through 103 by welding (e.g., Patent Document 1).

Patent Document 1: Japanese Patent No. 3530078

In the conventional particle measuring instrument, there is another means for measuring the particles in a liquid or a reactive gas in a floating condition using a flow cell such as quartz or sapphire. However, a limit of the sample pressure which is in practical use is 0.7 MPa due to withstand pressure limitations and the flow cell.

As one means for measuring particles floating in the high pressure gas (air/inert gas) of up to 1 MPa, there is a method for introducing a sample into a high pressure chamber (particle detecting area) through a nozzle without using the flow cell. However, this method cannot be applied in principle to the measurement of particles under a liquid phase, a reactive gas phase or a super critical phase because the sample mixes with an existing media (normally, air) within the chamber. Further, a mechanism with a nozzle may be complicated and it is also difficult to obtain withstand pressure performance above 1 MPa.

Referring to the method for measuring the particles by reducing the pressure using the regulator, disturbance such as dusting by the regulator is caused. Referring further to the liquid phase or super critical phase, if the pressure is reduced, since such a phase may not be maintained, it is necessary to measure the particles while maintaining the pressure.

SUMMARY OF THE INVENTION

It is therefore an object of the present invention to solve the problems as seen in the prior art and to provide a flow cell which can introduce a sample under high pressure into a measuring device, a method for manufacturing the flow cell, and a particle measuring instrument using the flow cell.

In order to attain this object, according to a first aspect of the present invention, a flow cell adapted to form a flow channel in which a measuring sample under high pressure is introduced, is provided, in which the flow channel has rounded corners in section.

According to a second aspect of the present invention, the flow cell adapted to form a flow channel in which a measuring sample under high pressure is introduced, is provided, in which the flow channel has a circular shape, a substantially circular shape or a rounded corner shape in section, and the length of the flow channel in the longitudinal direction is 10 times or more the maximum value of the bore diameter of the flow channel.

According to a third aspect of the present invention, a method for manufacturing a flow cell provided with a flow channel which has a circular shape, a substantially circular shape or a rounded corner shape in section, is provided, which comprises the steps of forming a groove, which has a semi-circular shape, a substantially semicircular shape or a rounded corner shape in section, on one surface of a block made of a transparent material, and joining two blocks, each being provided with the groove, to provide the flow channel.

According to a fourth aspect of the present invention, a particle measuring device is provided, which comprises the flow cell according to the first aspect or the second aspect, or the flow cell manufactured by the method according to the third aspect, wherein a measuring sample under high pressure is introduced into the flow channel formed in the flow cell, and particles floating in the measuring sample are measured.

According to a fifth aspect of the present invention, the particle measuring device according to the fourth aspect is provided, in which the measuring sample is in a liquid phase, a gaseous phase or a super critical phase above 1 MPa.

According to a sixth aspect of the present invention, the particle measuring instrument according to the fourth aspect or the fifth aspect is provided, in which a main component of the measuring sample is carbon dioxide.

BRIEF DESCRIPTION OF THE DRAWINGS

The above and other objects, features and advantages of the present invention will become more apparent from the following description when taken in conjunction with the accompanying drawings.

DETAILED DESCRIPTION OF THE PREFERRED EMBODIMENTS

Figure 1:
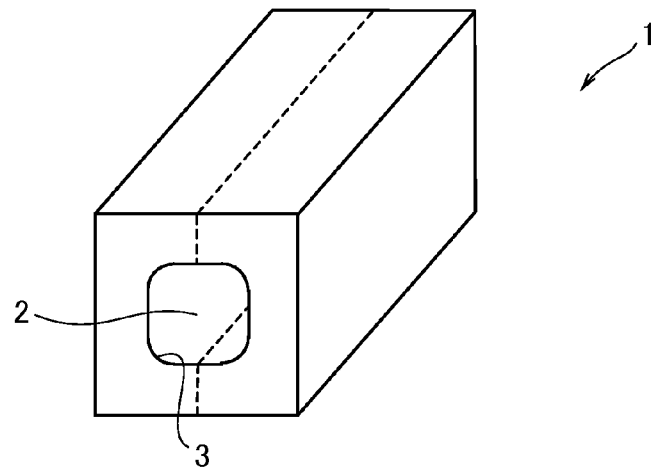
FIG. 1 is a perspective view of a first embodiment of a flow cell according to the present invention.
Figure 2:
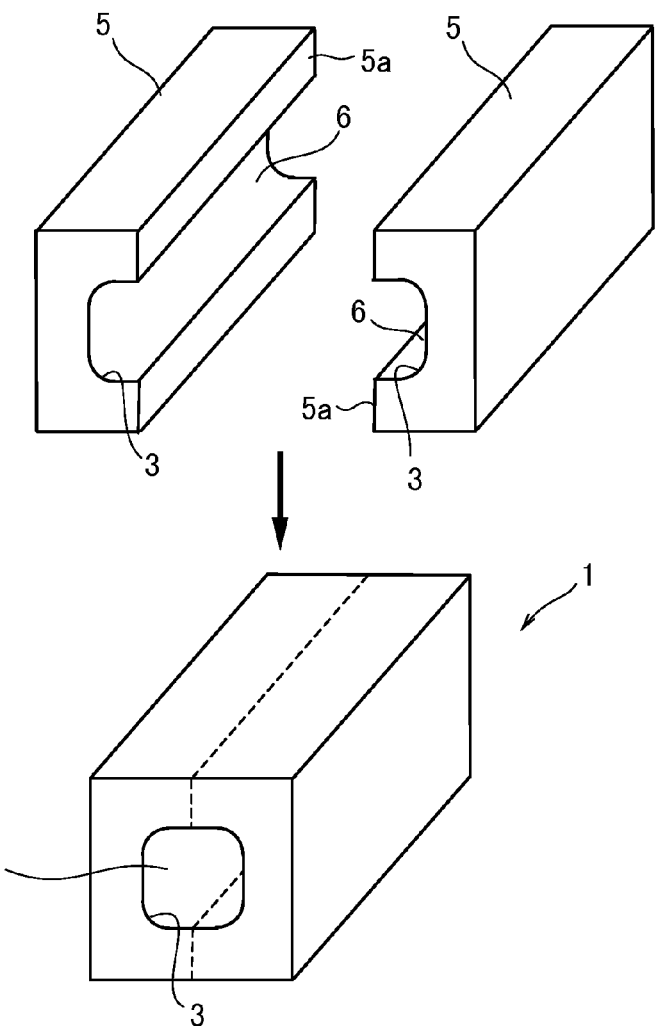
FIG. 2 is an explanatory view of a method for manufacturing the first embodiment of a flow cell according to the present invention.
Figure 3:
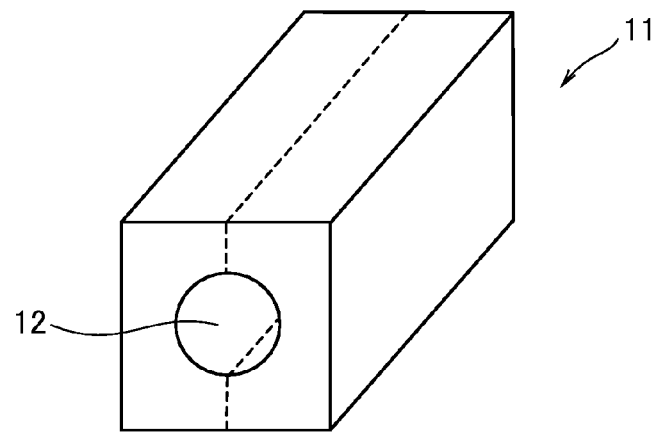
FIG. 3 is a perspective view of a second embodiment of a flow cell according to the present invention.
Figure 4:
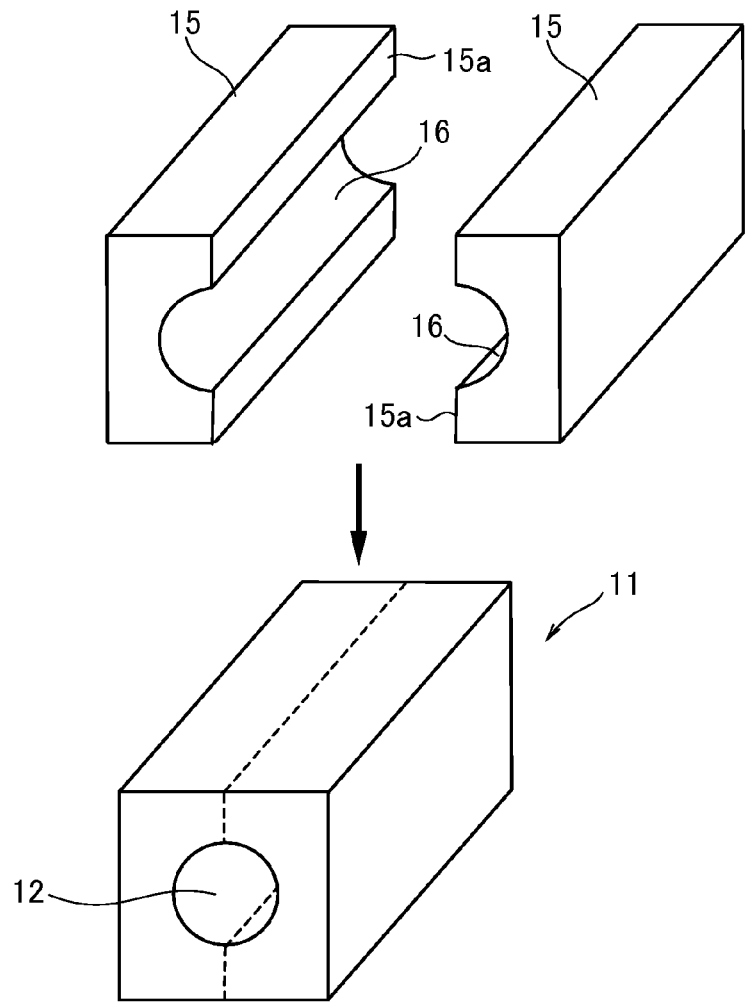
FIG. 4 is an explanatory view of a method for manufacturing the second embodiment of a flow cell according to the present invention.
Figure 5:
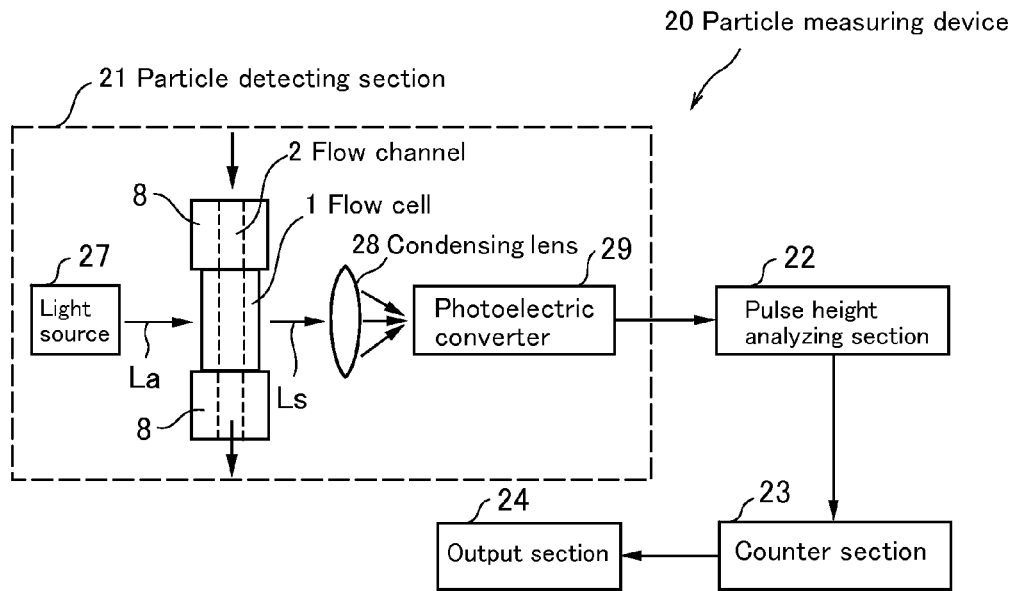
FIG. 5 is a schematic diagram of a particle measuring instrument according to the present invention.
Figure 6:
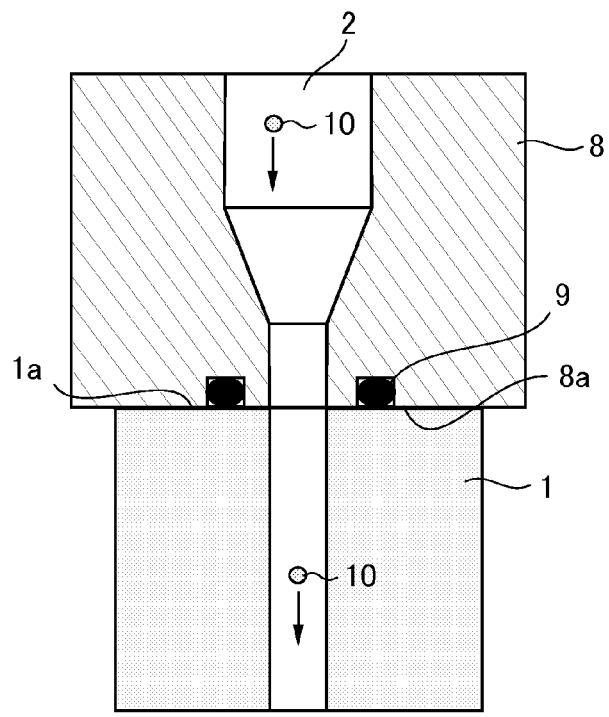
FIG. 6 is a cross-sectional view of a joint section of the flow cell with a metal pipe.
Figure 7:
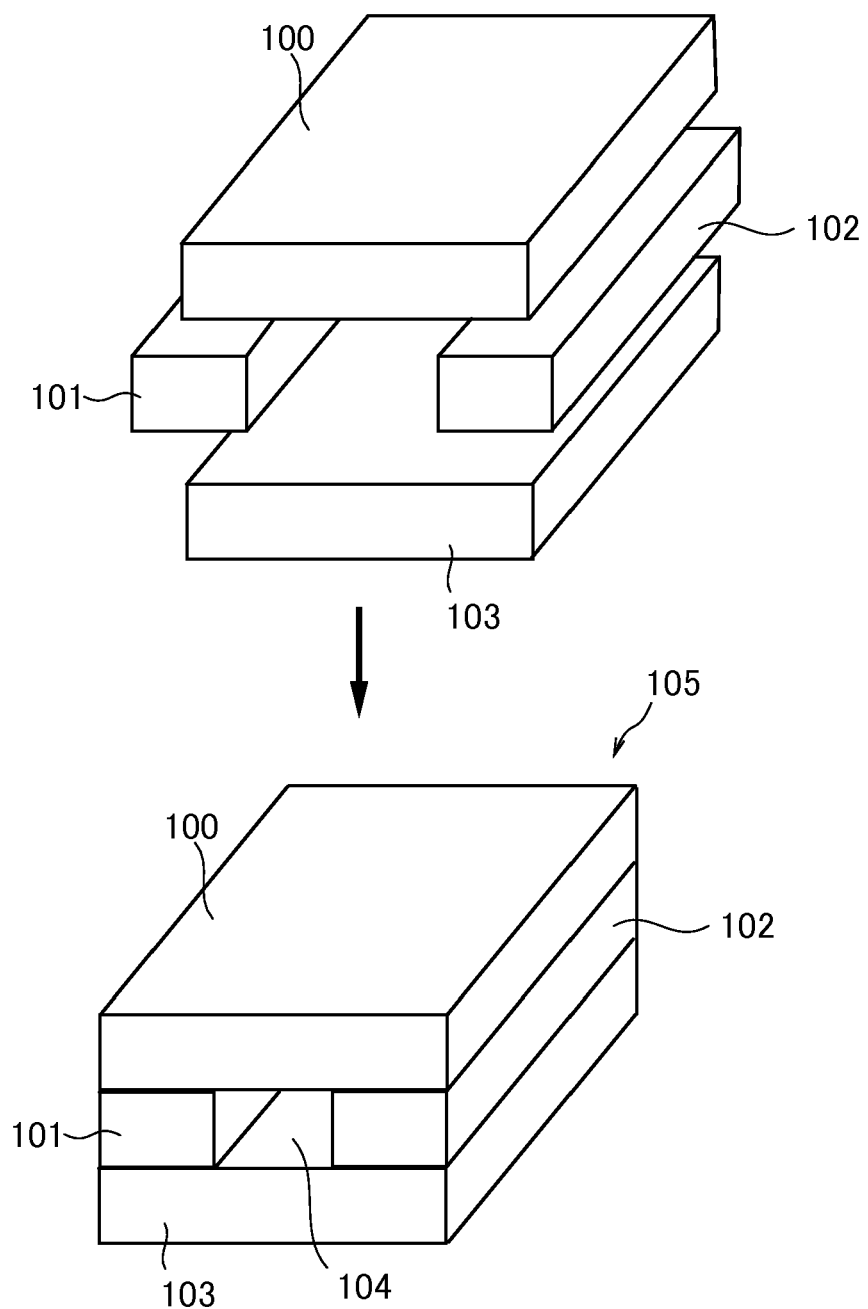
FIG. 7 is an explanatory view of a conventional flow cell manufacturing method.

A preferred embodiment of the present invention will now be described with reference to the accompanying drawings. FIG. 1 is a perspective view of a first embodiment of a flow cell according to the present invention and FIG. 2 is an explanatory view of a method for manufacturing the first embodiment of the flow cell. FIG. 3 is a perspective view of a second embodiment of the flow cell according to the present invention and FIG. 4 is an explanatory view of a method for manufacturing the second embodiment of the flow cell. FIG. 5 is a schematic diagram of a particle measuring instrument according to the present invention. FIG. 6 is a cross-sectional view of a joint section of the flow cell with a metal pipe.

As shown in FIG. 1, a flow cell 1 of a first embodiment is provided with a flow channel 2 of which the cross section is formed in a substantially quadrangular shape and which has four (4) rounded corners 3.

A method for manufacturing the flow cell 1 is shown in FIG. 2. A groove 6 of which the cross section is a quadrangle and which has two (2) rounded corners 3 (for example, R=0.1) is first formed on the largest surface 5a of a block 5 made of quartz which is a transparent material (groove forming process). Next, a wall surface of the groove 6 and the surface 5a are optically polished to provide a desired accuracy (polishing process). Two blocks 5 provided with such a groove 6 are made. The size of block 5 which is a rectangular parallelepiped is, for example, 10 mm×5 mm×30 mm, the width of the groove 6 is 0.5 mm, and the depth thereof is 0.25 mm.

Next, two blocks 5, each provided with the groove 6, are disposed so that the surfaces 5a and the grooves 6 face each other and the widths of the grooves 6 agree, wherein the two surfaces 5a are joined by adhesion to provide the flow channel 2 (joining process). Thus, the flow cell 1 having the flow channel 2 with a desired diameter is completed. The block 5 can also be made of a transparent material such as sapphire as well as the quartz. In the case of sapphire, the blocks are heated and joined at a lower temperature than the melting point while causing them to come into close contact.

After the joining process, a process (extension process) for heating the joined blocks 5, 5 to extend them in the longitudinal direction (i.e., flow channel direction) can be added to provide the flow channel 2 with a desired diameter. By adding this extension process, a flow channel with a smaller diameter can be readily formed and this also has an effect of cost reduction due to mass production. Although deterioration of the surface accuracy or striation is caused by the extension process, it has a sufficient effect if the deterioration is within an allowance of detection sensitivity.

FIG. 3 shows a flow cell 11 of a second embodiment, in which a flow channel 12 is formed of a circular shape in section.

A method for manufacturing the flow cell 11 is shown in FIG. 4. First, a groove 16 of a semicircular shape in section is formed on the largest surface 15a of a block 15 made of quartz which is a transparent material (groove forming process). Next, the wall surface of the groove 16 and the surface 15a are optically polished to provide a desired accuracy (polishing process). Two blocks 15, each provided with such a groove 16, are made. The size of block 15 which is a rectangular parallelepiped is, for example, 10 mm×5 mm×30 mm. The groove 16 is formed of a semicircular shape in section, of which the radius is 0.25 mm.

Next, two blocks 15, each provided with the groove 16, are disposed so that the surfaces 15a and the grooves 16 face each other and the widths of the grooves 16 agree, wherein the two surfaces 15a are joined by welding to provide the flow channel 12 (joining process). Thus, the flow cell 11 having the flow channel 12 with a desired diameter is completed. The block 15 can also be made of a transparent material such as sapphire as well as quartz. In the case of sapphire, the blocks are heated and jointed at a lower temperature than the melting point while causing them to come into close contact. An extension process can also be added after the joining process in the same manner as in the first embodiment.

A particle measuring instrument 20 according to the present invention using such a flow cell 1 is shown in FIG. 5. The particle measuring device 20 comprises a particle detecting portion 21 for detecting particles using light, a pulse height analyzing portion 22 for dividing the particle signals into the discrete particle size range, a counter portion 23 for counting the number of particles of every particle diameter range, and an output portion 24 for outputting the measurement results of the counter portion 23.

The particle detecting portion 21 comprises a flow channel 2 for flowing a measuring sample formed by the flow cell 1, a light source 27 for illuminating a laser beam La to the flow channel 2 to make a particle detecting area, a condensing lens 28 for condensing scattered light Ls scattered by the particles passing through the particle detecting area, and a photoelectric converter 29 for converting the scattered light condensed by the condensing lens 28 to a voltage corresponding to the intensity of the light. Reference numeral 8 designates a metal pipe for introducing the measuring sample into the flow channel 2.

The pulse height analyzing portion 22 receives an output signal from the particle detecting portion 21 and deems the signal above the predetermined level as to indicate a particle size corresponding to the level, thereby outputting the pulse to each channel according to the particle diameter segment. The counter portion 23 receives an output signal from the pulse height analyzing portion 22 and counts the pulse corresponding to the particle diameter range.

As shown in FIG. 6, the flow cell 1 is joined to the metal pipe 8 for introducing the sample into the flow channel 2 in the flow cell by O-ring 9 made of elastomer. A joint surface 8a of the metal piping 8 and a joint surface 1a of the flow cell 1 are provided to be parallel to each other, wherein the O-ring 9 is deformed to a certain compression level by the uniform force. With this arrangement, sufficient withstand pressure and leak prevention can be realized. Reference numeral 10 is a particle contained in the measuring sample. The flow cell 11 of which the flow channel 12 has a circular shape in section can be used in place of the flow cell 1 of which the flow channel 2 has a substantially quadrangular shape in section.

Operation of the particle measuring instrument 20 according to the present invention as constructed above will now be described. A main component of the measuring sample is carbon dioxide under a super critical state.

First, the measuring sample of which the main material is carbon dioxide which reached a super critical phase under pressure of about 20 MPa and at a temperature of 35° C. is introduced into the flow channel 2 of the particle measuring device 20 in the super critical phase. The measuring sample flows into the flow cell 1 along the flow channel 2. A laser beam La illuminated from the light source 27 reaches the flow channel 2 after passing through a quartz block forming the flow cell 1, illuminates against the particle floating in the measuring sample, and scatters. The scattered light Ls scattered by the particle is condensed by the condensing lens 28 and reaches the photoelectric converter 29. The voltage corresponding to the intensity of the light is output from the photoelectric converter 29.

Next, the pulse height analyzing portion 22 receives the output of the particle detecting portion 21 and outputs a pulse-shape signal to each channel according to the particle diameter range. The counter portion 23 receives an output signal from the pulse height analyzing portion 22, counts a pulse signal corresponding to the selected particle diameter range and outputs the results to the output portion 24.

The present particle measuring instrument 20 responds to the change of phase corresponding to the pressure of the measuring sample and can measure the particles contained in the measuring sample even in a gaseous phase, in a liquid phase or in a super critical phase. In the embodiments of the present invention, the main component of the measuring sample is the super critical carbon dioxide phase, but it is not limited to the carbon dioxide. The present particle measuring device 20 can measure the particles floating in the measuring sample even in the case of the gas phase or liquid phase under high pressure which is within the pressure range of about 1 MPa to 30 MPa. Referring to the flow cell as described in the first embodiment, it is confirmed that a pressure test was actually conducted under water of 30 MPa (50° C.) and as a result, the flow cell did not break, and no leakage from the flow parts was found.

It is to be noted that the present invention is not limited to the embodiments described above and various modifications and applications are possible within the spirit and scope of this invention as set forth in the appended claims. For example, the present invention is applied to the measuring device dedicated to particle measurement, but this is only one example. The present invention can also be applied to a general device for measuring the property of a fluid such as a chemical composition analyzer, a concentration meter, and a turbidity meter.

EFFECTS OF THE INVENTION

According to the first aspect of the present invention, a flow channel is formed of rounded corners in section and stress centering on the corners can be dispersed. In this manner, the flow cell is not broken even though a measuring sample is under high pressure.

According to the second aspect of the present invention, the flow cell is not broken even though the measuring sample is under high pressure. In the case where the flow cell is, for example, applied to a particle measuring instrument, it is easy to form a laminar flow condition in the flow channel because the flow channel is long. In the case of a long flow channel, it is easy to set a laser light source and as a result, the flow cell can be readily incorporated into a particle detecting instrument.

According to the third aspect of the present invention, a method for manufacturing the flow cell is provided by joining blocks, made of transparent material, each bock being provided with a groove. It is therefore possible to realize the finishing accuracy of grooving irrespective of the length of the flow channel.

According to the fourth aspect of the present invention, it is possible to measure particles in a high pressure fluid while keeping the high pressure condition. It is also possible to measure the particles floating in the fluid even though the condition of the measuring sample varies with the pressure change.

According to the fifth aspect of the present invention, it is possible to measure the particles contained in a high pressure fluid which is in a liquid phase, a gaseous phase or a super critical phase above 1 MPa.

According to the sixth aspect of the present invention, it is possible to measure the particles in a high pressure fluid of which the main material is carbon dioxide.

INDUSTRIAL APPLICABILITY

According to a particle measuring device of the present invention, it is possible to measure the particles contained in a high pressure fluid in a floating condition while keeping the high pressure phase. It is also possible to measure the particles contained in the fluid even though the state of the measuring sample varies with the pressure change. In this manner, it is expected to expand the scope of application as a particle measuring instrument.

What is claimed is:

1. A particle measuring instrument comprising a flow cell adapted to form a flow channel in which a measuring sample under high pressure is introduced, characterized in that the flow channel, formed by joining two blocks, has rounded corners in section, and further characterized in that the measuring sample under high pressure is introduced into the flow channel formed in the flow cell and particles floating in the measuring sample are measured, and, wherein the measuring sample is in a liquid phase, a gaseous phase or a super critical phase above 1 MPa.

2. The particle measuring instrument according to claim 1, wherein a main component of the measuring sample is carbon dioxide.

3. A particle measuring instrument comprising a flow cell adapted to form a flow channel in which a measuring sample under high pressure is introduced, characterized in that the flow channel, formed by joining two blocks, has rounded corners in section, and further characterized in that the measuring sample under high pressure is introduced into the flow channel formed in the flow cell and particles floating in the measuring sample are measured, and, wherein a main component of the measuring sample is carbon dioxide.

4. A particle measuring instrument comprising a flow cell adapted to form a flow channel by joining two blocks, in which a measuring sample under high pressure is introduced, characterized in that the flow channel has a circular shape, a substantially circular shape or a rounded corner shape in section, and the length of the flow channel in a longitudinal direction is 10 times or more a maximum value of the inside diameter of the flow channel, characterized in that a measuring sample under high pressure is introduced into a flow channel formed in the flow cell and particles floating in the measuring sample are measured, and, wherein a main component of the measuring sample is carbon dioxide.

5. A particle measuring instrument comprising a flow cell adapted to form a flow channel by joining two blocks, in which a measuring sample under high pressure is introduced, characterized in that the flow channel has a circular shape, a substantially circular shape or a rounded corner shape in section, and a length of the flow channel in a longitudinal direction is 10 times or more a maximum value of an inside diameter of the flow channel characterized in that the measuring sample under high pressure is introduced into the flow channel formed in the flow cell and particles floating in the measuring sample are measured, wherein the measuring sample is in a liquid phase, a gaseous phase or a super critical phase above 1 MPa and, wherein a main component of the measuring sample is carbon dioxide.

* * * * *